United States Patent
Drake

(10) Patent No.: US 9,730,598 B2
(45) Date of Patent: Aug. 15, 2017

(54) SYSTEMS AND METHODS FOR PERFORMING ELECTROCARDIOGRAMS

(71) Applicant: Stefan Drake, Los Angeles, CA (US)

(72) Inventor: Stefan Drake, Los Angeles, CA (US)

( * ) Notice: Subject to any disclaimer, the term of this patent is extended or adjusted under 35 U.S.C. 154(b) by 0 days.

(21) Appl. No.: 14/941,556

(22) Filed: Nov. 14, 2015

(65) Prior Publication Data
US 2016/0135701 A1 May 19, 2016

Related U.S. Application Data

(60) Provisional application No. 62/080,203, filed on Nov. 14, 2014.

(51) Int. Cl.
*A61B 5/04* (2006.01)
*A61B 5/0404* (2006.01)
*A61B 5/00* (2006.01)
*A61B 5/0408* (2006.01)
*A61B 5/0428* (2006.01)
*A61B 5/0432* (2006.01)
*A61B 5/044* (2006.01)

(52) U.S. Cl.
CPC .......... *A61B 5/0404* (2013.01); *A61B 5/0006* (2013.01); *A61B 5/044* (2013.01); *A61B 5/0408* (2013.01); *A61B 5/04012* (2013.01); *A61B 5/0428* (2013.01); *A61B 5/0432* (2013.01); *A61B 5/6898* (2013.01); *A61B 5/7475* (2013.01); *A61B 5/6824* (2013.01); *A61B 5/6828* (2013.01); *A61B 2560/0468* (2013.01)

(58) Field of Classification Search
CPC . A61B 5/0404; A61B 5/0408; A61B 5/04012; A61B 5/6824; A61B 5/6828
See application file for complete search history.

(56) References Cited

U.S. PATENT DOCUMENTS

| | | | | |
|---|---|---|---|---|
| 4,606,352 A | * | 8/1986 | Geddes | A61B 5/044 600/515 |
| 2009/0048496 A1 | * | 2/2009 | Fleischer | A61B 5/02405 600/301 |
| 2014/0114166 A1 | * | 4/2014 | Baxi | A61B 5/04085 600/384 |
| 2014/0276153 A1 | * | 9/2014 | Amitai | A61B 5/04028 600/509 |
| 2015/0018660 A1 | * | 1/2015 | Thomson | A61B 5/0404 600/393 |

* cited by examiner

*Primary Examiner* — Robert N Wieland
(74) *Attorney, Agent, or Firm* — Labyrinth Law PLLC; Kevin L. Miller

(57) ABSTRACT

A system for performing an electrocardiogram (ECG) can include a handheld electrocardiograph device having a right arm electrode, a left arm electrode, and a left leg electrode, and can be configured to receive signals from the electrodes and to send data based on the electrode signals to a mobile electronic device. The mobile electronic device can be configured to process and analyze the receive information to provide ECG data, such as 6-lead ECG data. The mobile electronic device can analyze the ECG data to provide diagnostic information. The mobile electronic device can transfer the ECG data to a remote computing system, which can analyze the ECG data to provide diagnostic information.

16 Claims, 6 Drawing Sheets

SYSTEMS AND METHODS FOR PERFORMING ELECTROCARDIOGRAMS

CROSS-REFERENCE TO A RELATED APPLICATION

This application claims the priority benefit of U.S. Provisional Application Ser. No. 62/080,203, filed Nov. 14, 2014, which is incorporated herein by reference in its entirety.

BACKGROUND OF THE INVENTION

The electrocardiogram (ECG or EKG) is recognized as one of the most successful and important tools for rapid, noninvasive assessments of cardiac conditions. The resting 12-lead ECG (standard 12-lead ECG) recordings have been used to determine cardiac conditions in the presence of conflicting or ambiguous clinical symptoms. A 12-lead ECG can be obtained by attaching 10 electrodes to a patient: 4 limb lead electrodes are attached to limbs (left and right wrist, left and right ankle) and 6 precordial lead electrodes are attached to the torso. This configuration allows for recording leads I, II, Vi leads (where i=1 to 6), and calculating leads III, aVR, aVL and aVF. Electrocardiographs can be used to display/print ECG waveforms and for generating clinical statements based on diagnostic criteria derived from ECG measurements. Interpretation of an ECG is performed by electrocardiogram waveform analysis and can sometimes be performed by a serial comparison of a current ECG to a previously recorded ECG.

However, the resting 12-lead ECG obtained in the hospital or doctor's office can have limitations imposed by the recording environment. Everyday life, exercise, stress and a number of physiological conditions can elicit cardiac problems that can be masked or are not present during recordings on the human body at rest. Therefore, a stress test and ambulatory recordings can be used as additional sources of information on cardiac status. During a stress test, limb electrodes can be moved to the torso to reduce noise and artifacts caused by movement of long wires, muscle activity, and unstable electrode-skin interface.

Moreover, the acquisition of cardiac signals from a patient while in a non-hospital setting can be hampered by a variety of circumstances. To obtain high-quality ECG recordings, the electrode-skin interface needs to be stable, otherwise noise and artifacts can distort the recording of signals. Furthermore, in some situations, it is impractical to attach electrodes and wires to the body of a patient in motion. In ambulatory settings, it can be impractical to record with a large number of wires, so a small recorder can be used to record only a few ECG channels.

BRIEF SUMMARY OF THE INVENTION

Systems and techniques are disclosed for obtaining electrocardiogram recordings with a portable handheld device that enables obtaining 6-lead electrocardiogram data. Obtaining 6-lead electrocardiogram data requires a device capable of recording leads I and II simultaneously in standard ECG mode. Such recordings require connection of the device with a patient's left arm, right arm, and left leg, therefore various embodiments disclosed herein relate to electrocardiograph devices that can have three electrodes (e.g., three dry electrodes). To obtain recordings, left and right hand device electrodes can be held by left and right hands and the third electrode can be pressed against the left leg. The device's third electrode can be pressed against the skin, for example, just above the knee or above the ankle.

In some embodiments, 3-electrode electrocardiograph devices can be coupled with mobile electronic devices that can provide 6-lead electrocardiogram data. In some cases, a mobile electronic device can display user interface elements configured to output information based on the 6-lead electrocardiogram data. In certain embodiments, a remote computing system may receive the 6-lead electrocardiogram data and provide diagnostic information.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION OF THE INVENTION

Figure 1:
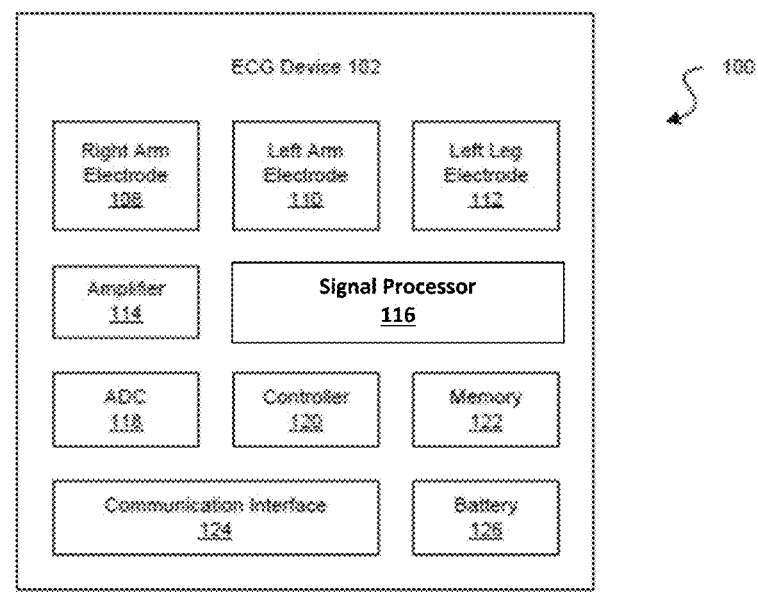
FIG. 1 shows an example embodiment of a system for performing electrocardiogram (ECG or EKG) recordings.
Figure 1:
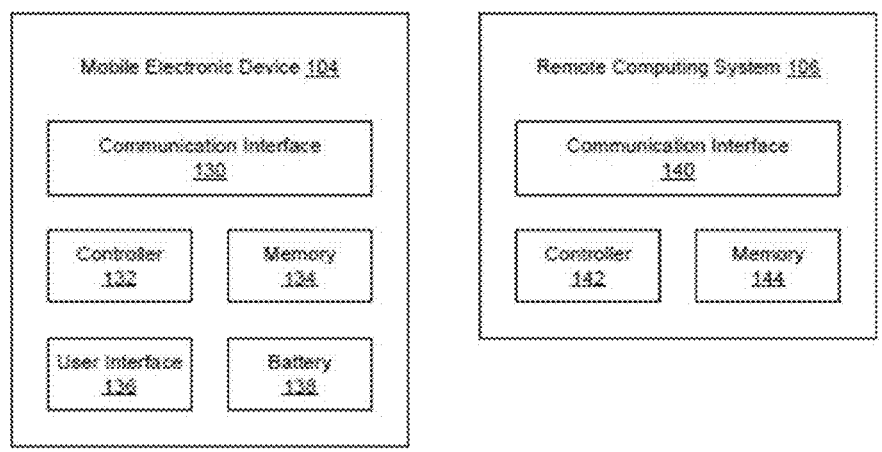

Various embodiments disclosed herein relate to a portable handheld electrocardiograph device with three dry electrodes allowing for recordings of left arm (LA), right arm (RA) and left leg (LL) signals, which can be used to obtain 6 ECG leads (I, II, III, aVR, aVF, and aVL), as discussed herein. Various embodiments relate to medical instrumentation and information systems. A handheld electrocardiographic device, as disclosed herein, can provide the ability to record limb leads and auxiliary limb leads (e.g., 6 leads total) from subjects in ambulatory settings, which can be comparable the 12 leads recorded using a standard 12-lead electrocardiograph in hospital settings.

Use of a presently available single-lead handheld ECG device in ambulatory settings has limited diagnostic value compared to 12-lead ECG recorders. It can provide basic heart monitoring and it can be useful for characterizing various arrhythmias. When a recording is made between the left and right hand, it represents lead I (I=LA-RA) and it is equivalent to only lead I of a standard 12-lead ECG.

A device capable of recording leads I and II simultaneously in standard ECG mode would increase diagnostic yield compared to using a single-lead device. As recordings of lead II (II=LL−RA) requires connection of the device to the left leg, various embodiments disclosed herein relate to ECG devices that can have three electrodes (e.g., three dry electrodes). To obtain recordings, device left and right hand electrodes can be held by the subject's left and right hands and the third electrode can be pressed against the left leg. The device's third electrode can be pressed against the skin, for example, just above the knee or above the ankle.

ECG signals I and II obtained from electrodes can be amplified and digitized (e.g., by a microcontroller with an internal analog-to-digital converter. Data can then be transferred (e.g., via serial interface and Bluetooth module) to a mobile electronic device (e.g., a cellular phone) for initial display and storage. The mobile electronic device (e.g., a cellular phone) can perform initial processing and transmit data to a remote computing system (e.g., an ECG server or ECG cloud service) for interpretation, serial comparison, and analysis.

Various embodiments disclosed herein can relate to a handheld electrocardiographic device for simultaneous acquisition of six leads (limb leads and auxiliary limb leads). The device can include three dry electrodes for obtaining ECG signals I and II from a subject. Signals I and II can be obtained in the same manner as on a traditional 12-lead electrocardiograph. Leads III and auxiliary leads aVR, aVL and aVF can be calculated (e.g., based on Leads I and II). To emphasize ambulatory use, the conventional wet electrodes (usually silver-silver chloride Ag/AgCl) and skin preparation that hospitals use are replaced with dry electrodes requiring no skin preparation.

Lead I is defined as LA–RA, and can be obtained by holding the device's left and right electrodes with both the left and right hands while the device is faced down. Lead II is defined as LL–RA. Lead II can be obtained by holding the device with both the left and right hands while simultaneously pressing the third electrode against the skin just above the subject's knee or ankle.

The electrodes can be connected to amplifiers. The input of the amplifiers can be designed to accept signals from the dry electrodes. The output of the amplifiers can be connected to an analog-to-digital converter (ADC). Digital data from the ADC can be connected to a microcontroller. Data from the microcontroller can be sent to a communication interface (e.g., a Bluetooth interface) for transmission to a mobile electronic device (e.g., a cellular phone). The mobile electronic device can be used for initial data evaluation and/or to transfer data to a remote computing system (e.g., an ECG server). The data on the remote computing system (e.g., ECG server) can be evaluated (e.g., by automatic algorithms) and the diagnosis/results can be sent to the end user or to a doctor or other medical professional.

FIG. 1 shows an example of a system 100 for performing electrocardiogram (ECG or EKG) recordings according to some embodiments. The system 100 can be configured to perform a 6-lead ECG. The system 100 can include an electrocardiograph (ECG) device 102 and a mobile electronic device 104, and in some embodiments the system 100 can include a remote computing system 106. The ECG device 102 can include three electrodes, such as a right arm electrode 108, a left arm electrode 110, and a left leg electrode 112. In some embodiments, the system 100 can use fewer electrodes than a traditional 12-lead ECG, which would use ten electrodes, which can facilitate performance of the ECG procedure, especially for ECG procedures performed by a patient himself or herself. The system 100 can be configured to perform an ECG procedure (e.g., a 6-lead ECG) without using a right leg electrode, a V1 electrode, a V2 electrode, a V3 electrode, a V4 electrode, a V5 electrode, or a V6 electrode, which would ordinarily be used for a traditional 12-lead ECG. The system 100 can be configured to perform the ECG procedure using only the three electrodes 108, 110, and 112.

In some embodiments, the electrodes 108, 110, and 112 can be dry electrodes, which can be configured to be used by a patient without applying a gel between the electrodes and the skin and/or with little or no skin preparation (e.g., shaving, cleaning, sanding, etc.). In some embodiments, the use of dry electrodes can result in higher impedance, and the system 100 (e.g., with amplifier 114) can be configured to compensate for the higher impedance that can result from the use of dry electrodes instead of wet electrodes, which would generally be used for a traditional 12-lead ECG. In some embodiments, the electrodes 108, 110, and 112 can be made of stainless steel (e.g., low-carbon stainless steel such as 316L grade stainless steel). Various other conductive materials can be used for the electrodes 108, 110, and 112, such as gold, silver, copper, aluminum, metal alloys, and various other suitably conductive materials.

In some embodiments, one or more wet electrodes can be used, but the use of dry electrodes can facilitate the performance of quick ECG recording procedures, especially those performed by the patient using a mobile device without direct involvement of a medical professional.

The ECG device 102 can include one or more amplifiers 114 configured to amplify signals (e.g., analog signals) from the electrodes 108, 110, and 112. In some embodiments, each electrode 108, 110, and 112 has a corresponding amplifier 114 that is configured to amplify the signals from that electrode. In some embodiments, a single amplifier 114 can amplify the signals from two or all three of the electrodes 108, 110, and 112. The one or more amplifiers 114 can be configured to amplify the signals to compensate for impedance, which may be produced, e.g., by the use of dry electrodes.

The ECG device 102 can include a signal processor 116, which can be configured to perform one or more signal processing operations on the signals received from the right arm electrode 108, from the left arm electrode 110, and from the left leg electrode 112 (e.g., on the amplified analog signals output by the one or more amplifiers 114). In some cases, the signal processor 116 can be configured to perform analog signal processing operations. In some embodiments, the signal processor 116 can be configured to compare and calculate signals from the different electrodes 108, 110, and 112. For example, a first lead (Lead I) can be based at least in part on a voltage difference measured (e.g., by the signal processor 116) between the left arm electrode 110 and the right arm electrode 108, and a second lead (Lead II) can be based at least in part on a voltage difference measured (e.g., by the signal processor 116) between the left leg electrode 112 and the right arm electrode 108.

In some embodiments, the signal processor 116 can be configured to perform one or more signal processing operations to improve the signal-to-noise ratio for the signals. In some embodiments, the signal processor 116 can be configured to perform one or more signal processing operations to remove or reduce baseline wander. In some embodiments, the signal processor 116 can be configured to perform one or more signal processing operations to compensate for impedance (e.g., produced by the use of dry electrodes).

The ECG device 102 can include an analog-to-digital converter (ADC) 118, which can be configured to convert analog signals (e.g., received from the signal processor 116, from the one or more amplifiers 114, or directly from the electrodes 108, 110, and 112) to digital signals.

The ECG device 102 can include a controller 120. The controller 120 can be a processor or processing system as described herein. In some embodiments, the ECG device 102 can include memory 122, which can store executable program instructions that can be executed by the controller 120 to implement various methods, operations, and features described herein. Memory 122 can be a type of computer readable storage media as described herein. In some embodiments, the controller 120 can store data to the memory 122. For example, data corresponding to the digital signals received over time can be stored on the memory 122 for use in signal processing operations that depend on previous signals. Results of signal processing and/or data analysis can be stored in the memory 122, and can be accessed by the controller 120 be used for later calculations. In some embodiments, data received and/or generated (e.g., by the controller 120) can be stored on the memory 122 so that it can be periodically transmitted by the communication interface 124 (e.g., as packets of data).

In some embodiments, the controller 120 can be a digital controller and can be configured to receive digital signals (e.g., digital signals output by the ADC). The controller 120 can receive, for example, digital representations of the signals from the right arm electrode 108, the left arm electrode 110, and the left leg electrode 112, or of the amplified (from 114) and/or signal-processed (from 116) versions of the original analog signals from the electrodes 108, 110, and 112.

The controller 120 can receive separate signals corresponding to the three electrodes 108, 110, and 112, or the controller 120 can receive signals that represent information from different combinations of the electrodes 108, 110, and 112 (e.g., signals associated with the voltage differences between electrodes). For example, in some embodiments, the controller 120 can receive a digital signal representing a voltage difference between the left arm electrode 110 and the right arm electrode 108 and a digital signal representing a voltage difference between the left leg electrode 112 and the right arm electrode 108.

The controller 120 can perform one or more signal processing operations (e.g., digital signal processing on the digital signals received). The controller 120 can perform one or more digital signal processing operations to remove or reduce baseline wander, to improve the signal-to-noise ratio, to compensate for impedance (e.g., produced by the use of dry electrodes), etc. In some embodiments, the controller 120 can perform one or more linear phase filtering operations (e.g., recursive or non-recursive linear phase filtering).

The controller 120 can analyze the signals received by the controller 120. For example, the controller 120 can compare and analyze signals corresponding to the different electrodes 108, 110, and 112, for example, to determine a voltage difference between the left arm electrode 110 and the right arm electrode 108 (Lead I) and/or to determine a voltage difference between the left leg electrode 112 and the right arm electrode 108 (Lead II). In some embodiments, the controller 120 can determine the 6 leads for a 6-lead ECG, as discussed herein.

Figure 7:
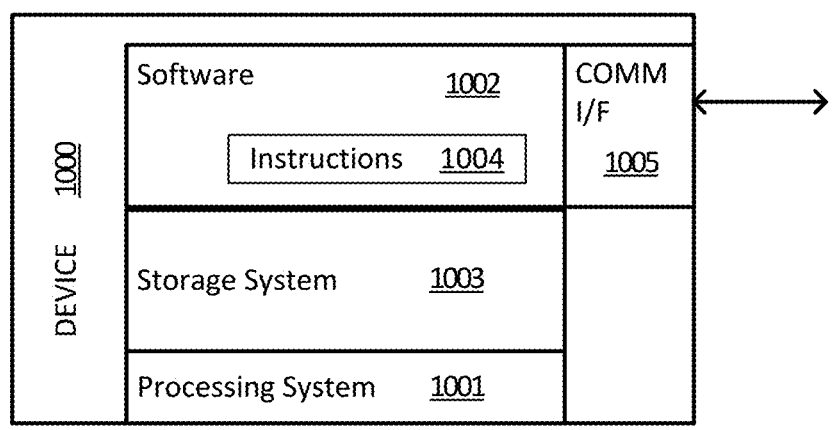
FIG. 7 shows a block diagram illustrating components of a computing device or system used in some implementations of systems and techniques for performing an electrocardiogram.

The ECG device 102 can include a communication interface 124, which can be configured to enable the ECG device 102 to communicate with other communication interfaces to coupled interpretive devices, e.g., the communication interface 130 on the mobile electronic device 104, the communication interface 140 on the remote computing system 106, and/or other external systems for reporting results (e.g., a hospital information system, and a doctor email system). The controller 120 can send data to the communication interface 124 for transmission to coupled interpretive devices and/or external devices and systems. The communication interfaces 124, 130, and 140 described herein can be wireless communication interfaces as described with respect to device 1000 (FIG. 7). Communication interfaces 124, 130, and 140 can include, for example, Wi-Fi, Bluetooth, Bluetooth Low Energy (BLE), near field communication (NFC), 3G, and 4G. In some embodiments, the communication interface 124, 130, 140 can use a wire or cable or physical communication port to communicate data. For example, the ECG device 102 can include an electrical connector (e.g., a micro-USB connector or lightning connector) that is configured to engage a corresponding port on the mobile electronic device 104 (e.g., a micro-USB port or lightning port), or on another external device or system, to communicate information between the devices and/or systems. Other communication methods can be used as well. For example, the communication interfaces 124, 130, and 140 can be configured to transfer data via an audio input port or microphone.

The ECG device 102 can be a portable device, such as an accessory for use with the mobile electronic device 104. The ECG device 102 can include a battery 126, which can facilitate the portable nature of the ECG device 102. Other power sources can be used. For example, the ECG device 102 can receive electrical power from an external power source (e.g., a wall outlet), or a battery 138 of the mobile electronic device 104 can supply electrical power to the ECG device 102, for instance, when the ECG device 102 and the mobile electronic device 104 are coupled via a wire or cable (e.g., via a micro-USB or lightning connection) or passive charging system.

The mobile electronic device 104 can be a mobile phone (e.g., a smart phone), a tablet computer, a laptop computer, or other computing device. The mobile electronic device 104 can include a communication interface 130 as discussed. The communication interface 130 can be configured to send and/or receive information to and/or from the ECG device 102 (e.g., via a first communication protocol, which can have a relatively short range, such as Bluetooth, BLE, or NFC). The communication interface 130 can be configured to send and/or receive information to and/or from a remote computing system 106 (e.g., using a second communication protocol, which can have a relatively long range, such as Wi-Fi, 3G, 4G, TCP/IP over Ethernet, the Internet, etc.). In some embodiments, the mobile electronic device 104 can operate as a middleman to relay information between the ECG device 102 and the remote computing system 106 (or another external device or system).

The mobile electronic device 104 can include a controller 132. The controller 132 can be a processor or processing system as described herein. In some embodiments, the mobile electronic device 104 can include memory 134, which can store executable instructions that can be executed by the controller 132 to implement various methods, operations, and features described herein. In some embodiments, the controller 132 can store data to the memory 134. For example, data corresponding to the digital signals received over time can be stored on the memory 134 for use in signal processing operations that depend on previous signals. Results of signal processing and/or data analysis can be stored in the memory 134, and can accessed by the controller 132 to be used for later calculations. In some embodiments, data received and/or generated (e.g., by the controller 132) can be stored on the memory 134, such as for archiving, for later reference, or to be periodically transmitted by the communication interface 130 (e.g., as packets of data). Memory 134 can be a type of computer readable storage media as described herein.

In some embodiments, the controller 132 can run an application or program (which can be stored on memory 134), which can perform the ECG processing, as described herein. In some embodiments, an application or program can run remotely (e.g., on the remote computing system 106, using cloud computing, or as Software as a Service (SaaS)) to perform the ECG procedure.

The controller 132 can be configured to perform one or more signal processing operations (e.g., digital signal processing) on the data received from the ECG device 102. The controller 132 can perform one or more digital signal processing operations to remove or reduce baseline wander, to improve the signal-to-noise ratio, to compensate for impedance (e.g., produced by the use of dry electrodes), etc. In some embodiments, the controller 132 can perform one or more linear phase filtering operations (e.g., recursive or non-recursive linear phase filtering).

The controller 132 can analyze data (e.g., received from the ECG device 102). For example, the controller 132 can compare signals corresponding to the different electrodes 108, 110, and 112, for example, to determine a voltage difference between the left arm electrode 110 and the right arm electrode 108 (Lead I) and/or to determine a voltage difference between the left leg electrode 112 and the right arm electrode 108 (Lead II).

In some embodiments, the controller 132 can determine the 6 leads for a 6-lead ECG, as discussed herein. The controller 132 can provide a 6-lead ECG having three limb leads: Lead I, Lead II, and Lead III, and three augmented limb leads: augmented vector right (aVR), augmented vector left (aVL), and augmented vector foot (aVF). The 6 leads can be represented by the following equations:

Lead $I$=LA−RA;

Lead $II$=LL−RA;

Lead $III$=LL−LA;

Augmented vector right(aVR)=RA−½(LA+LL);

Augmented vector left(aVL)=LA−½(RA+LL); and

Augmented vector foot(aVF)=LL−½(RA+LA).

In the equations above, LA can correspond to a voltage of the left arm electrode 110, RA can correspond to a voltage of the right arm electrode 108, and LL can correspond to a voltage of the left leg electrode 112. In some embodiments, the system 100 does not produce the precordial leads, which would normally be produced by a 12-lead ECG.

In some embodiments, Lead III, aVR, aVL, and aVF can be calculated based on Lead I and Lead II, as set forth in the following equations (wherein "I" corresponds to Lead I and "II" corresponds to Lead II):

Lead $III$=$II$−$I$;

aVR=−($I$+$II$)/2;

aVL=$I$−$II$/2; and aVF=$II$−$I$/2.

In some embodiments, the controller 132 can perform analysis on the ECG data (e.g., the 6-lead ECG data) to determine a heart rate, to make a determination of normal heart rhythm, and/or to diagnose one or more disorders. In some embodiments, data, algorithms, and methods that are established for analysis of 12-lead ECG data can be used to analyze the 6-lead ECG data (which can include 6 of the same leads as a traditional 12-lead ECG).

The mobile electronic device 104 can include a user interface 136, which can be configured to receive input from a user and/or to output information to a user. In some embodiments, the user interface 136 can include one or more user input elements (e.g., buttons, switches, etc.), a microphone (e.g., for receiving dictated instructions), a display, a touchscreen display, a speaker, etc. The user interface 136 can receive an instruction (e.g., via input from a user) to initiate an ECG recording procedure. The communication interface 130 of the mobile electronic device 104 can send an instruction to the ECG device 102 to initiate the ECG procedure. The user interface 136 can provide instructions to a user for performing the ECG or related activities (e.g., to hold or touch the electrodes 108, 110, and 112, to wait during a delay period or while signals are collected, to contact a doctor or emergency services, etc.). The user interface 136 can report information to a user (e.g., a heart rate, an ECG tracing, an indication of normal rhythm, a diagnosis, etc.).

The mobile electronic device can include a battery 138, which can facilitate the portable nature of the mobile electronic device 104. Other power sources can be used. For example, the mobile electronic device 104 can receive electrical power from an external power source (e.g., a wall outlet).

The communication interface 130 of the mobile electronic device 104 can be configured to send ECG data (e.g., 6-lead ECG data) to the remote computing system 106 (using the communication interface 140), as discussed herein. The remote computing system 106 can be a server, a computer, or other computing system.

The remote computing system 106 can include a controller 142. The controller 142 can be a processor or processing system as described herein. In some embodiments, the remote computing system 106 can include memory 144, which can store executable program instructions that can be executed by the controller 142 to implement various methods, operations, and features described herein. Memory 144 can be a type of computer readable storage media as described herein. In some embodiments, the controller 142 can store data to the memory 144. For example, data corresponding to the digital signals received over time can be stored on the memory 144 for use in signal processing operations that depend on previous signals. Results of signal processing and/or data analysis can be stored in the memory 144, and can be accessed by the controller 142 be used for later calculations. In some embodiments, data received and/or generated (e.g., by the controller 142) can be stored on the memory 144, such as for archiving, for later reference, etc. In some embodiments, the controller 142 can run an application or program (which can be stored on memory 144), which can perform the ECG procedure (e.g., using cloud computing, or as Software as a Service (SaaS)).

The controller 142 of the remote computing system 106 can execute program instructions for performing an analysis on the ECG data (e.g., the 6-lead ECG data), which can be received from the mobile electronic device 104, for example, to determine a heart rate, to make a determination of normal heart rhythm, and/or to diagnose one or more disorders.

In some embodiments, data, algorithms, and methods that are established for analysis of 12-lead ECG data can be used to analyze the 6-lead ECG data (which can include 6 of the same leads as a traditional 12-lead ECG). In some embodiments, the remote computing system 106 may have access to data and program instructions (e.g., stored in memory 144) that are not directly accessible to the mobile electronic device 104 and/or more resources such as more powerful processor(s), so that the remote computing system 106 can perform more thorough analysis on the ECG data than would be performed on the mobile electronic device 104. In some embodiments, the mobile electronic device 104 can perform an initial analysis (which can be performed relatively quickly on the local device) on the ECG data to make one or more initial determinations (e.g., regarding diagnosis and rhythm analysis), and the remote computing system 106 can perform a more detailed analysis (which may take longer time due to transmission of data, backlog of analysis requests, complexity of algorithms for data analysis, and/or the volume of calculations needed for the detailed analysis).

In some implementations, the controller 142 of the remote computing system 106 can be used to perform various signal processing and data analysis tasks described herein (e.g., digital signal processing, improvement of signal-to-noise ratio, removal or reduction of baseline wander, compensation for impedance, linear phase filtering, providing a 6-lead ECG), especially for embodiments where an application or program that performs the ECG procedure runs on the remote computing system 106 (e.g., using cloud computing or SaaS).

In some embodiments, the ECG device 102 can have a relatively low power processor (e.g., controller 120) as compared to the processor(s) of the mobile electronic device 104 and/or the remote computing system 106 (e.g., controllers 132 and 142), and the ECG device 102 can have more limited resources (e.g., less battery power, less memory storage, etc.) than the mobile electronic device 104 and/or the remote computing system 106. Accordingly, in some implementations, the system 100 is configured to minimize or reduce the operations performed by the ECG device 102 and may preferentially perform operations on the mobile electronic device 104 and/or the remote computing system 106.

In some embodiments, the ECG device 102 can be configured to perform the digital signal processing and analysis, as discussed herein, because the signals are converted to digital data before being transmitted from the ECG device 102. In some embodiments, the ECG device 102 is configured to perform operations to reduce the amount of data to be transferred by the communication interface 124, which can save power and time during the transfer of data from the ECG device 102. For example, in some embodiments, the ECG device 102 is configured to send data corresponding to two voltage differences (leads I and II) instead of sending data corresponding to three signals from the three electrodes 108, 110, and 112. Any or all of these variations of raw, transformed, or interpreted signal data may be referred to as "signal-related data."

The system 100 shown and described in connection with FIG. 1 can be modified in various ways. For example, in some embodiments, the ECG device 102 and the mobile electronic device 104 can be combined into a single device (which can be a dedicated ECG and mobile device). In some embodiments, an ECG system can include a single device that performs the functions of the ECG device 102, the mobile electronic device 104, and the remote computing system 106 (e.g., a 6-lead ECG machine such as for use in a hospital or doctor's office). Embodiments of a combined ECG system may include fewer components than three separate devices to eliminate redundancy (e.g., controller 120, 132, and 142 may be combined into a single controller, communication interface 124, 130, and 140 into a single communication interface, etc.).

Figure 2:
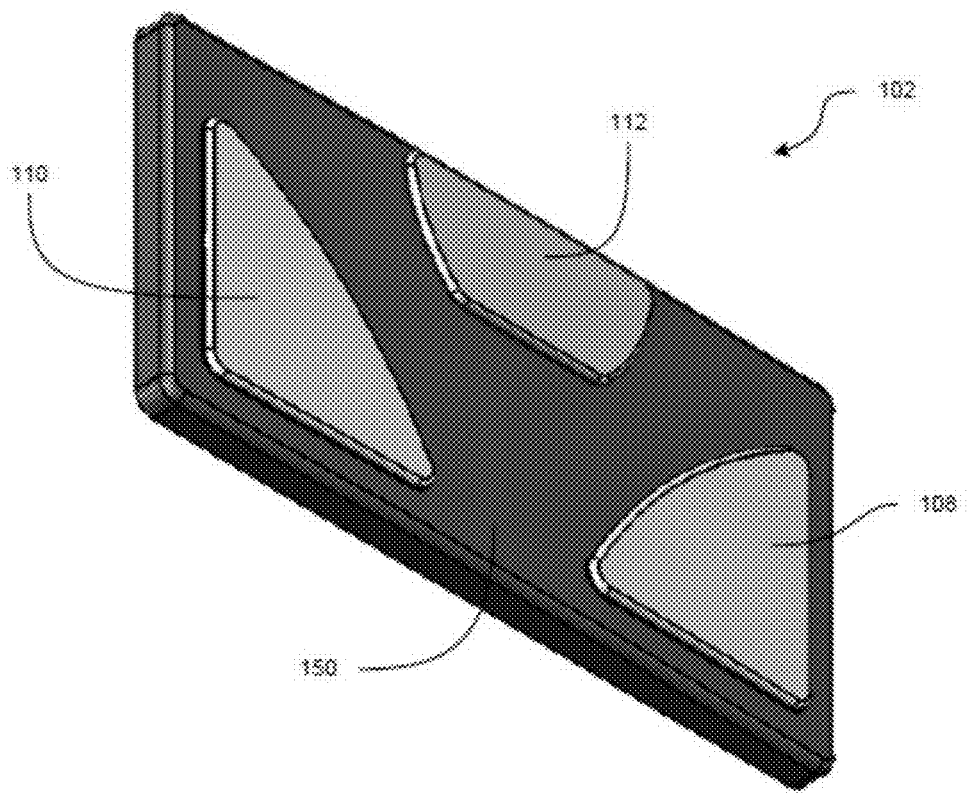
FIG. 2 shows an example embodiment of a handheld electrocardiograph device.

FIG. 2 shows an example embodiment of an ECG device 102. The ECG device 102 can include a housing 150, which can house or enclose various components of the ECG device 102 (e.g., the one or more amplifiers 114, the signal processor 116, the analog-to-digital converter 118, the controller 120, the memory 122, the communication interface 124, and the battery 126). The ECG device 102 can include the right arm electrode 108, the left arm electrode 110, and the left leg electrode 112, which can be exposed to facilitate contact to the patient's skin. The electrodes 108, 110 and 112 can be positioned on the bottom of the housing 150. The right arm electrode 108 can be positioned on a right side to facilitate contact to the patient's right arm or hand. The left arm electrode 110 can be positioned on a left side to facilitate contact to the patient's left arm or hand. The left leg electrode 112 can be positioned in a central portion, to facilitate contact to the patient's left leg (e.g., to the left knee, left ankle, or left foot). The left leg electrode 112 can be positioned closer to the patient than the right arm electrode 108 and/or the left arm electrode 110, when the electrodes face downward with the right arm electrode 108 on the right and the left arm electrode 110 on the left, which can reduce undesired contact between the electrodes 108, 110, and 112 with undesired parts of the patient's body and/or can reduce undesired contact between the parts of the patient's body being monitored, which could interfere with the readings for the ECG procedure.

In some embodiments, the right arm electrode 108 and the left arm electrode 110 may be positioned differently, e.g., in reverse of the configuration shown in FIG. 2. This positioning may vary in accordance with the chosen placement of the left leg electrode 112 of the device on the left leg, for example, on the dorsal or ventral sides of the left leg. In some embodiments, the designation of the pads as right arm electrode 108 and left arm electrode 110 may be selectable or configurable by the user, for instance via a user interface provided on the ECG device 102 or the mobile electronic device 104.

In some embodiments, mobile electronic device 104 can include a user interface that can receive input from the user to assign or reassign one of the three electrodes to a particular limb. The designation can then be transmitted, in some cases, to the ECG device 102 via a communication interface (e.g., 124, 130) to associate a particular electrode to a limb reading. Advantageously, a user may be able to reassign the function of a physical electrode to a limb designation that is more comfortable to the user for gathering a particular signal. For example, if the user is more comfortable reading the left leg signal from the dorsal (rear) side of the leg, then the right and left arm electrodes may be assigned to the right and left electrodes, respectively, when the ECG device 102 is facing up. On the other hand, if the user is more comfortable reading the left leg signal from the ventral (front) side of the leg, then the right and left arm electrodes may be assigned to the left and right electrodes (i.e., opposite), respectively, when the ECG device 102 is facing up.

In some embodiments, the electrodes 108, 110, and 112 can be positioned immovably on the housing and immovably with respect to each other. In some embodiments, the ECG device 102 does not include wires or cables outside of the housing 150 that couple to the electrodes 108, 110, and 112. The electrodes 108, 110, and 112 can be positioned close to each other to facilitate the portable and compact nature of the ECG device 102, and the electrodes 108, 110, and 112 can be spaced apart sufficiently to reduce the likelihood of unintended contact between the electrodes 108, 110, and 112 (e.g., such as a body part contacting two or more of the electrodes simultaneously). The electrodes 108, 110, and 112 can be spaced apart by a distance that is at least about 3 mm, at least about 5 mm, at least about 10 mm, at least about 25 mm, at least about 50 mm or more, less than or equal to about 100 mm, less than or equal to about 75 mm, less than or equal to about 50 mm, less than or equal to about 25 mm, less than or equal to about 10 mm or less, although values outside these ranges can be used in some instances.

Figure 3:
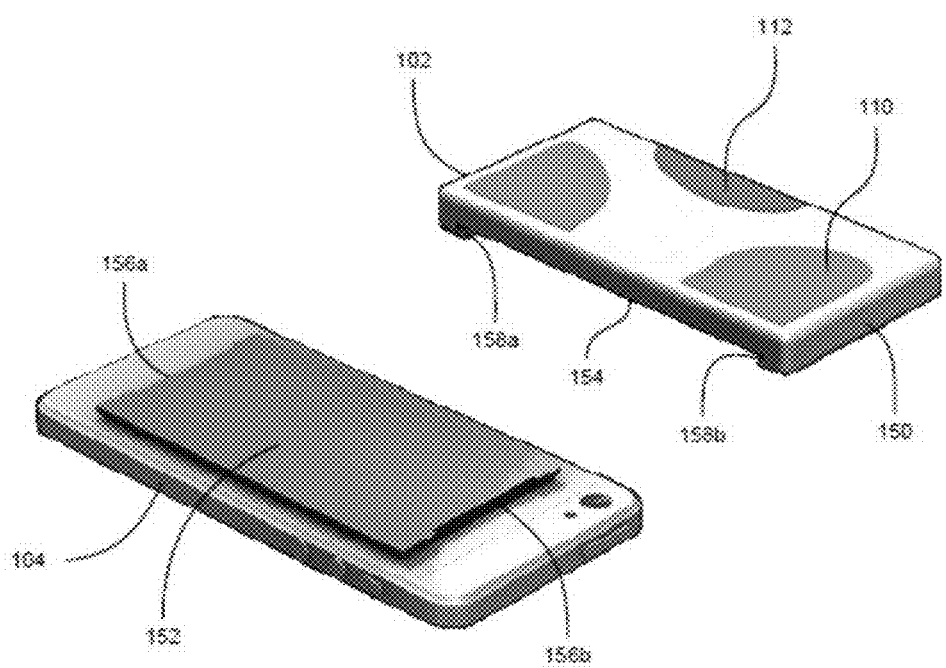
FIG. 3 shows an example embodiment of a handheld electrocardiograph device that is removably attached to a mobile electronic device.

FIG. 3 shows an example embodiment of an ECG device 102 that is removably attachable to a mobile electronic device 104 (e.g., a smart phone). The mobile electronic device 104 can include an attachment mechanism 152, which can be configured to interface with an attachment mechanism 154 on the ECG device 102 to removably attach the ECG device 102 to the mobile electronic device 104 (e.g., onto the back side of the mobile electronic device 104 such as on a side opposite the display on a smart phone). The attachment mechanisms 152 and 154 can use sliding engagement, a snap fit, a clamp, etc. to removably couple the ECG device 102 to the mobile electronic device 104. In some embodiments, only one or the other of the ECG device 102 and the mobile electronic device 104 may include an attachment mechanism. In the embodiment illustrated in FIG. 3, the attachment mechanism 152 can include rails or guides 156a and 156b (e.g., formed at the sides of a raised platform) that are configured to slidably engage rails or guides 158a and 158b (e.g., formed at the sides of a recessed slot in the housing 150). Various alternatives are possible for the attachment mechanisms. For example, in some embodiments, the ECG device 102 can be incorporated into a protective case that is configured to enclose at least a portion of the mobile electronic device 104.

Figure 4:
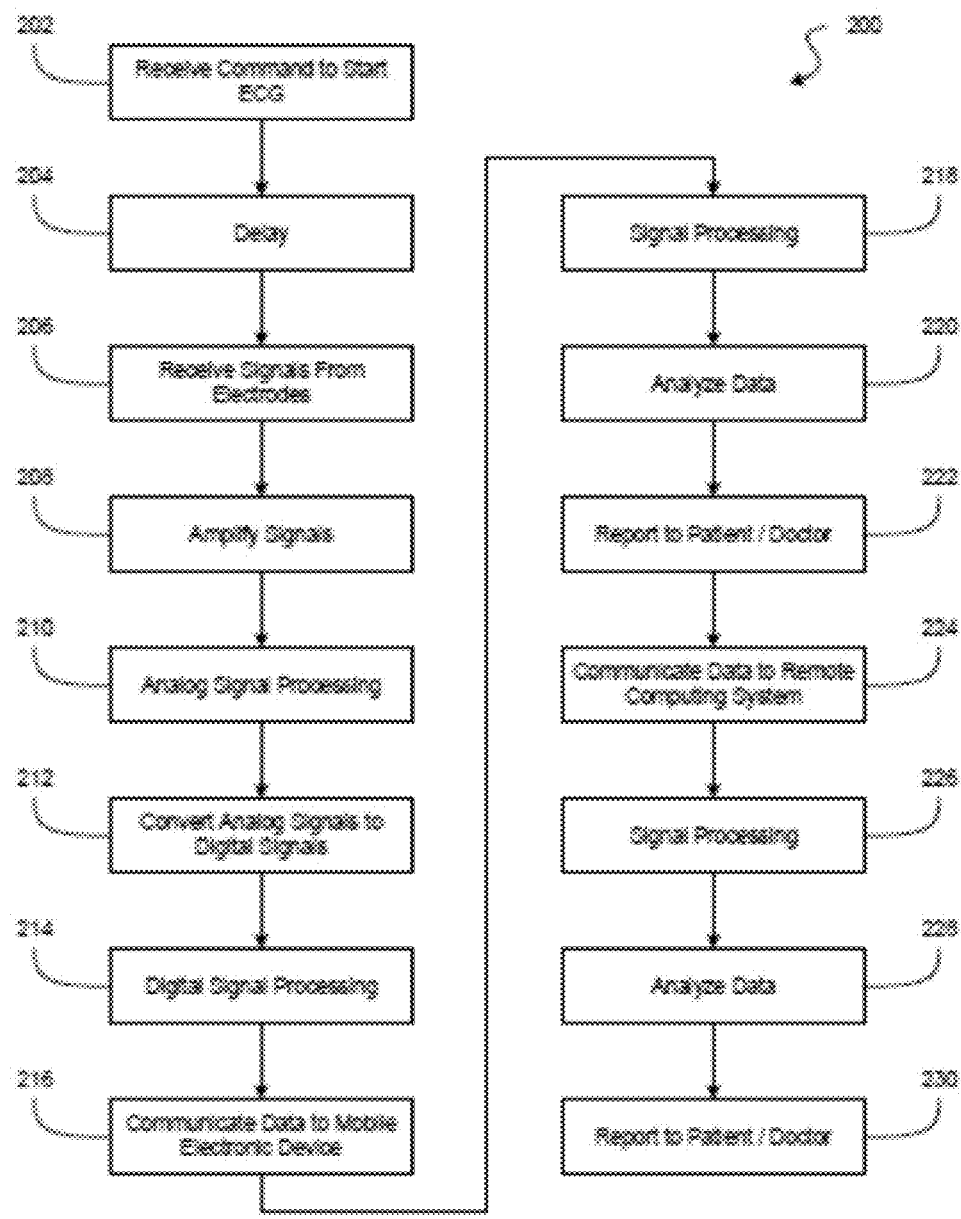
FIG. 4 shows a flow chart of an example method for performing electrocardiogram recordings.

FIG. 4 is a flowchart of an example method 200 of operation for performing an ECG procedure in accordance with some embodiments herein. At block 202, the system can receive a command (e.g., from a user, which can be the patient) to start an ECG procedure. The command from the user can be received by the user interface 136 on the mobile electronic device, although in some embodiments, the ECG device can include a user input element configured to receive a user command to start an ECG procedure. In some embodiments, the ECG device 102 can receive an instruction to start an ECG procedure from the mobile electronic device 104 (e.g., via the communication interfaces 124 and 130). At block 204, the method 200 can include a delay, which can give the user time to position the electrodes 108, 110, and 112 into contact with the proper body portions (e.g., since the patient can be the user that issued the start command such as by pressing a button on the mobile electronic device 104). The delay can be between about 1 and about 10, between about 2 seconds and about 5 second, or about 3 seconds, although other amounts of delay outside these ranges can be used in some instances. In some cases the delay may terminate when the user issues a continue command, e.g., by interacting with an element of the user interface on the touchscreen of the mobile electronic device 104 or by pressing a button on the housing of 104 or ECG device 102.

At block 206, signals from the electrodes 108, 110, and 112 can be received, as discussed herein. At block 208, the signals from the electrodes 108, 110, and 112 can be amplified, as discussed herein. The amplification can compensate for impedance (such as produced by the use of dry electrodes). The amplification can be performed on analog signals received from the electrodes 108, 110, and 112.

At block 210, analog signal processing can be performed, such as described in connection with the signal processing module 116. At block 212, the analog signals can be converted to digital signals, such as by the analog-to-digital converter 118, as discussed herein. At block 214, digital signal processing can be performed, such as by the controller 120, as discussed herein.

At block 216, the ECG device 102 can communicate data (e.g., raw or interpreted data, depending on embodiment) to the mobile electronic device 104 (e.g., via the communication interfaces 124 and 130). At block 218, the mobile electronic device 104 can perform signal processing on the received data, as discussed herein. At block 220, the mobile electronic device 104 can perform data analysis, such as to produce ECG data (e.g., 6-lead ECG data), to analyze the data to provide a heart rate, to provide a determination of normal or abnormal heart rhythm, and/or to provide a diagnosis of a heart disorder. At block 222, information can be reported (e.g., to the user/patient, to a doctor, or other entity such as a hospital information system). The memory 134 can include information to facilitate reporting to external devices and systems, such as a doctor email address, hospital information system access information, etc.) In some information, information can be reported to a user via the user interface 136 on the mobile electronic device 104.

At block 224, data can be communicated to a remote computing system 106 (e.g., via the communication interfaces 130 and 140). In some embodiments, the ECG data (e.g., 6-lead ECG data) can be transmitted to the remote computing system 106, for example, for further processing and/or analysis (blocks 226 and 228). In some embodiments, the mobile electronic device 104 can send information to the remote computing system 106 regarding initial determinations made by the analysis performed by the mobile electronic device 104, and the remote computing system 106 can perform additional analysis to confirm or refute the initial determinations made by the mobile electronic device 104. At block 230, information, including concerning an additional analysis, can be reported (e.g., to the user/patient, to a doctor, or to another entity such as a hospital information system). The memory 144 at the remote computing system 106 can include information to facilitate reporting to external devices and systems, such as a doctor email address, hospital information system access information, etc. Reporting information can be transferred from the remote computing system 106 to the mobile electronic device 104 (via the communication interfaces 130 and 140) for reporting to the user (e.g., via the user interface 136). Many variations are possible. For example, various operations shown and described in connection with FIG. 4 can be omitted, combined with other operations, or separated into sub-operations, and additional operations can be added.

Figure 5:
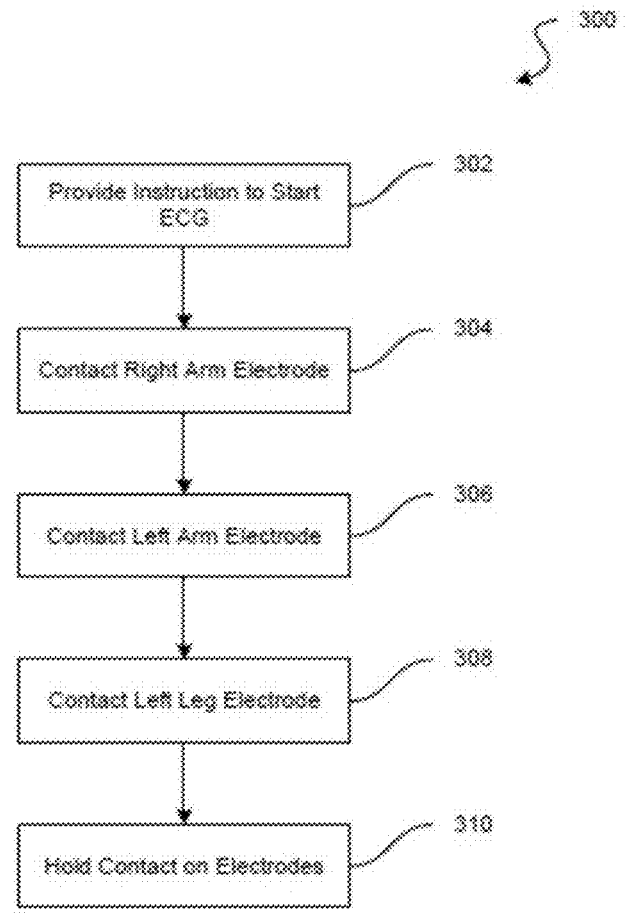
FIG. 5 shows a flow chart of an example method of operating an electrocardiogram system.

FIG. 5 is a flowchart showing an example embodiment of a method of use 300 for an ECG system. At block 302, the user can provide an instruction to start an ECG procedure (e.g., via the user interface 136 on the mobile electronic device 104). At block 304, the user can contact the right atm electrode 108 to a portion of the user's right arm, such as by holding the ECG device 102 with a right thumb or finger on the right arm electrode 108. At block 306, the user can contact the left arm electrode 110 to a portion of the user's left arm, such as by holding the ECG device 102 with a left thumb or finger on the left arm electrode 110. At block 308, the user can contact the left leg electrode 112 to a portion of the user's left leg, such as by holding the ECG device 102 such that the left leg electrode 112 contacts the user's left leg (e.g., at the left knee or left ankle). At block 310, the user can hold the contact with the electrodes 108, 110, and 112 for the duration of the ECG procedure, for example, until instructed via the user interface 136 that the procedure is completed such as with a visual, auditory, or tactile signal from the mobile electronic device 104 or ECG device 102.

Figure 6:
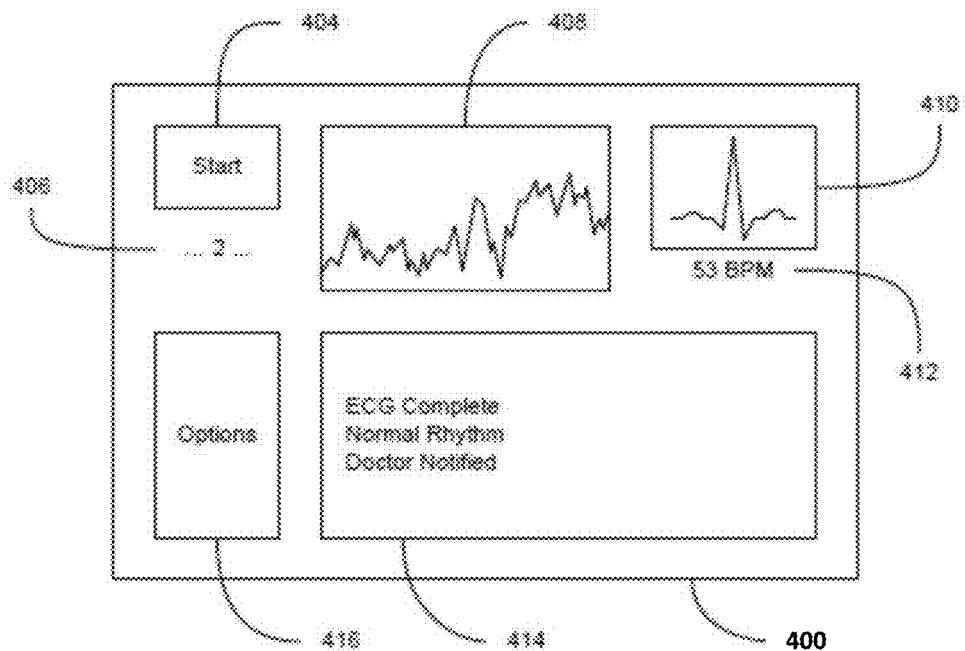
FIG. 6 shows an example embodiment of a user interface for an electrocardiogram system.

FIG. 6 shows an example embodiment of a user interface 400 for an ECG system, which can be used, for example, for the user interface 136, described herein. The user interface can be implemented on a display, such as a touch screen display, of a mobile electronic device 104. The user interface 400 can include a user input element (e.g., a digital button on a touch screen display) for initiating an ECG procedure, such as a start button 404. The user interface 400 can include a notification element 406 to notify the user of a delay period after receipt of a command to start an ECG procedure, such as a displayed count down from 3 to 2 to 1. The user interface 400 can include an ECG tracing portion 408, which can be configured to show ECG tracing information during the ECG procedure, which can alert the user that the ECG procedure is being performed. In some embodiments, the ECG tracing portion 408 can display information that is unprocessed or only partially processed, which can result in the ECG tracing portion displaying a graphical representation that does not necessarily look like a normal ECG waveform, but which can inform the user that the system is successfully gathering information from the electrodes 108, 110, 112. The user interface 400 can include an ECG waveform portion 410, which can display a processed ECG tracing (e.g., for a single beat). The processed ECG tracing shown by portion 410 can be an average or weighted average based on some or all of the ECG data that was collected and processed. The user interface 400 can display heart rate information 412. The user interface 400 can include a reporting portion for displaying commands or reports for the user. For example, as shown in element 414, the reporting portion can report to the user that the ECG process was completed, that a determination of normal heart rhythm was determined, and that the user's doctor was notified. The user interface 410 can have an options section 416, which can enable the user to change various options and parameters of the system. For example, the user can set an email address or other contact information for a doctor to be notified of ECG results, the user can change the delay time, etc.

FIG. 7 shows a block diagram illustrating components of a computing device or system used in some implementations of techniques and systems for performing an electrocardiogram as described herein. For example, components of the system, including an electrocardiograph device, mobile electronic device, and/or remote computing system may be implemented as described with respect to device 1000. Device 1000 can itself include one or more computing devices. The hardware can be configured according to any suitable computer architectures such as Symmetric Multi-Processing (SMP) architecture or Non-Uniform Memory Access (NUMA) architecture.

The device 1000 can include a processing system 1001, which may include a processing device such as a central processing unit (CPU) or microprocessor and other circuitry that retrieves and executes software 1002 from storage system 1003. Processing system 1001 may be implemented within a single processing device but may also be distributed across multiple processing devices or sub-systems that cooperate in executing program instructions. A controller, such as might be found on one or more system devices, can be a processing system or processor as described herein.

Examples of processing system 1001 include general purpose central processing units, application specific processors, and logic devices, as well as any other type of processing device, combinations, or variations thereof. The one or more processing devices may include multiprocessors or multi-core processors and may operate according to one or more suitable instruction sets including, but not limited to, a Reduced Instruction Set Computing (RISC) instruction set, a Complex Instruction Set Computing (CISC) instruction set, or a combination thereof. In certain embodiments, one or more digital signal processors (DSPs) may be included as part of the computer hardware of the system in place of or in addition to a general purpose CPU.

Storage system 1003 may comprise any computer readable storage media readable by processing system 1001 and capable of storing software 1002 including, e.g., processing instructions performing an electrocardiogram as described herein. Storage system 1003 may include volatile and non-volatile, removable and non-removable media implemented in any method or technology for storage of information, such as computer readable instructions, data structures, program modules, or other data.

Examples of storage media include random access memory (RAM), read only memory (ROM), magnetic disks, optical disks, CDs, DVDs, flash memory, solid state memory, phase change memory, 3D-XPoint memory, or any other suitable storage media. Certain implementations may involve either or both virtual memory and non-virtual memory. In no case do storage media consist of a propagated signal. In addition to storage media, in some implementations, storage system 1003 may also include communication media over which software 1002 may be communicated internally or externally.

Storage system 1003 may be implemented as a single storage device but may also be implemented across multiple storage devices or sub-systems co-located or distributed relative to each other. Storage system 1003 may include additional elements capable of communicating with processing system 1001.

Software 1002 may be implemented in program instructions and, among other functions, may, when executed by device 1000 in general or processing system 1001 in particular, direct device 1000 or processing system 1001 to operate as described herein for performing an electrocardiogram. Software 1002 may provide program instructions 1004 that implement components for performing an electrocardiogram. Software 1002 may implement on device 1000 components, programs, agents, or layers that implement in machine-readable processing instructions 1004 the methods and techniques described herein.

In general, software 1002 may, when loaded into processing system 1001 and executed, transform device 1000 overall from a general-purpose computing system into a special-purpose computing system customized to perform an electrocardiogram in accordance with the techniques herein. Indeed, encoding software 1002 on storage system 1003 may transform the physical structure of storage system 1003. The specific transformation of the physical structure may depend on various factors in different implementations of this description. Examples of such factors may include, but are not limited to, the technology used to implement the storage media of storage system 1003 and whether the computer-storage media are characterized as primary or secondary storage. Software 1002 may also include firmware or some other form of machine-readable processing instructions executable by processing system 1001. Software 1002 may also include additional processes, programs, or components, such as operating system software and other application software.

Device 1000 may represent any computing system on which software 1002 may be staged and from where software 1002 may be distributed, transported, downloaded, or otherwise provided to yet another computing system for deployment and execution, or yet additional distribution. Device 1000 may also represent other computing systems that may form a necessary or optional part of an operating environment for the disclosed techniques and systems, e.g., remote computing system or mobile electronic device.

A communication interface 1005 may be included, providing communication connections and devices that allow for communication between device 1000 and other computing systems (not shown) over a communication network or collection of networks (not shown) or the air. Examples of connections and devices that together allow for inter-system communication may include network interface cards, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned communication media, network, connections, and devices are well known and need not be discussed at length here.

It should be noted that many elements of device 1000 may be included in a system-on-a-chip (SoC) device. These elements may include, but are not limited to, the processing system 1001, a communications interface 1005, and even elements of the storage system 1003 and software 1002.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules. In some cases, one or more capabilities, e.g., the processing system, storage system, and communication interface may be included on a single device such as a microcontroller.

Furthermore, while certain types of user interfaces and controls are described herein for illustrative purposes, other types of user interfaces and controls may be used. A user interface may be generated on a local computer or on a mobile device, or it may be generated from a service or cloud server and sent to a client for rendering, e.g., in a browser or "app."

Certain aspects of the invention provide the following non-limiting embodiments:

Example 1

A system for performing an electrocardiogram comprising: an electrocardiograph device, comprising: a housing comprising three electrodes, wherein the three electrodes are not coupled to the device with wires exterior to the housing; a communication interface; one or more computer readable storage media; program instructions stored on the one or more computer readable storage media that, when executed by a controller, direct the controller to: receive signals from the three electrodes; analyze the signals to determine signal-related data; transmit the signal-related data, via the communication interface, to a coupled interpretive device.

Example 2

The system of example 1, wherein the electrocardiograph device is a portable handheld device.

Example 3

The system of any of examples 1-2, wherein the electrocardiograph device further comprises: one or more amplifiers configured to amplify analog signals received from the three electrodes; and program instructions stored on the one or more computer readable storage media that, when executed by the controller, direct the controller to receive and analyze amplified analog signals from the one or more amplifiers.

Example 4

The system of any of examples 1-3, wherein the electrocardiograph device further comprises: an analog signal processor configured to perform analog signal processing on analog signals received from the three electrodes; and program instructions stored on the one or more computer readable storage media that, when executed by the controller, direct the controller to receive and analyze processed analog signals from the analog signal processor.

Example 5

The system of any of examples 1-4, wherein the electrocardiograph device further comprises: an analog-to-digital converter configured to convert analog signals from the three electrodes to digital signals; and program instructions stored on the one or more computer readable storage media that, when executed by the controller, direct the controller to receive and analyze the digital signals from the analog-to-digital converter.

Example 6

The system of any of examples 1-5, wherein the electrocardiograph device further comprises program instructions stored on the one or more computer readable storage media that, when executed by the controller, direct the controller to perform digital signal processing on the signals received from the three electrodes.

Example 7

The system of any of examples 1-6, further comprising: a mobile electronic device comprising: a second communication interface; second program instructions stored on second computer readable storage media that, when executed by second controller, direct the second controller to: receive the signal-related data transmitted by the communication interface of the electrocardiograph device; and provide 6-lead electrocardiogram data based at least in part on the data received by the second communication interface.

Example 8

The system of example 7, wherein the 6-lead electrocardiogram data includes Lead I, Lead II, Lead III, aVR, aVL, and aVF.

Example 9

The system of any of examples 7-8, wherein the mobile electronic device further comprises program instructions stored on the second computer readable storage media that, when executed by the second controller, direct the second controller to: display user interface elements configured to receive input from a user to initiate an electrocardiogram procedure; and in response to receiving the input from the user, sending an instruction to the electrocardiograph device to initiate the electrocardiogram procedure.

Example 10

The system of example 9, wherein the system delays sending the instruction to initiate the electrocardiogram procedure by a delay time after receiving the input from the user.

Example 11

The system of any of examples 7-10, wherein the mobile electronic device further comprises program instructions stored on the second computer readable storage media that, when executed by the second controller, direct the second controller to: display user interface elements configured to output information based on the 6-lead electrocardiogram data.

Example 12

The system of any of examples 7-11, further comprising a remote computing system comprising: third program instructions stored on third computer readable storage media that, when executed by third controller, direct the third controller to: receive the 6-lead electrocardiogram data provided from the mobile electronic device; and analyze the 6-lead electrocardiogram data; and provide diagnostic information.

Example 13

The system of example 12, wherein the mobile electronic device further comprises program instructions stored on the second computer readable storage media that, when executed by the second controller, direct the second controller to: receive the diagnostic information provided from the remote computing system; and display user interface elements configured to output the diagnostic information provided from the remote computing system.

Example 14

The system of any of examples 7-13, wherein the electrocardiograph device is removably attached to the mobile electronic device.

Example 15

The system of any of examples 1-14, wherein the signal-related data includes 6-lead electrocardiogram data comprising Lead I, Lead II, Lead III, aVR, aVL, and aVF.

Example 16

The system of any of examples 1-15, wherein the three electrodes are fixed immovably to the outside of the housing of the electrocardiograph device.

Example 17

The system of any of examples 1-16, wherein the three electrodes comprise dry electrodes.

Example 18

The system of any of examples 17, wherein the electrocardiograph device further comprises program instructions stored on the one or more computer readable storage media that, when executed by the controller, direct the controller to compensate for higher impedance of the dry electrodes.

Example 19

The system of any of examples claim 1-18, wherein the three electrodes comprise a right arm electrode, a left arm electrode, and a left leg electrode.

Example 20

The system of any of examples 7-18, wherein the mobile electronic device further comprises program instructions stored on the second computer readable storage media that, when executed by the second controller, direct the second controller to: display user interface elements configured to receive input from a user to assign each of the three electrodes to a particular limb; and in response to receiving the input from the user, sending an instruction to the electrocardiograph device to associate readings from each of the three electrodes to the particular limb.

The embodiments discussed herein are provided by way of example, and various modifications can be made to the embodiments described herein. Certain features that are described in this disclosure in the context of separate embodiments can also be implemented in combination in a single embodiment. Conversely, various features that are described in the context of a single embodiment can be implemented in multiple embodiments separately or in various suitable subcombinations. Also, features described in connection with one combination can be excised from that combination and can be combined with other features in various combinations and subcombinations. Various features can be added to the example embodiments disclosed herein. Also, various features can be omitted from the example embodiments disclosed herein.

Similarly, while operations are depicted in the drawings or described in a particular order, the operations can be performed in a different order than shown or described. Other operations not depicted can be incorporated before, after, or simultaneously with the operations shown or described. In certain circumstances, parallel processing or multitasking can be used. Also, in some cases, the operations shown or discussed can be omitted or recombined to form various combinations and subcombinations.

The invention claimed is:

1. An apparatus for performing an electrocardiogram comprising:
   a housing comprising three electrodes, wherein the three electrodes are not coupled to the apparatus with wires exterior to the housing, wherein the three electrodes are disposed on a single surface of the housing;
   an attachment mechanism for removably attaching the housing to a mobile device;
   a communication interface;
   one or more computer readable storage media;

program instructions stored on the one or more computer readable storage media that, when executed by a controller, direct the controller to:
receive signals from the three electrodes;
analyze the signals to determine signal-related data; and
transmit the signal-related data, via the communication interface, to the mobile device.

2. The apparatus of claim 1, further comprising:
one or more amplifiers configured to amplify analog signals received from the three electrodes; and
program instructions stored on the one or more computer readable storage media that, when executed by the controller, direct the controller to receive and analyze amplified analog signals from the one or more amplifiers.

3. The apparatus of claim 1, further comprising:
an analog signal processor configured to perform analog signal processing on analog signals received from the three electrodes; and
program instructions stored on the one or more computer readable storage media that, when executed by the controller, direct the controller to receive and analyze processed analog signals from the analog signal processor.

4. The apparatus of claim 1, further comprising:
an analog-to-digital converter configured to convert analog signals from the three electrodes to digital signals; and
program instructions stored on the one or more computer readable storage media that, when executed by the controller, direct the controller to receive and analyze the digital signals from the analog-to-digital converter.

5. The apparatus of claim 1, further comprising:
second program instructions stored on second computer readable storage media that, when executed by a second controller in the mobile device, direct the second controller to:
receive the signal-related data transmitted by the communication interface; and
provide 6-lead electrocardiogram data based at least in part on the signal-related data.

6. The apparatus of claim 5, further comprising program instructions stored on the second computer readable storage media that, when executed by the second controller, direct the second controller to:
display user interface elements configured to receive input from a user to initiate an electrocardiogram procedure; and
in response to receiving the input from the user, sending an instruction via the communication interface to initiate the electrocardiogram procedure.

7. The apparatus of claim 6, wherein the user interface elements allow the user to set a configurable delay time for initiating the electrocardiogram procedure, and wherein the mobile device delays the sending of the instruction to initiate the electrocardiogram procedure by the configurable delay time.

8. The apparatus of claim 5, further comprising program instructions stored on the second computer readable storage media that, when executed by the second controller, direct the second controller to:
display user interface elements configured to output information based on the 6-lead electrocardiogram data.

9. The apparatus of claim 5, wherein further comprising program instructions stored on the second computer readable storage media that, when executed by the second controller, direct the second controller to:
display user interface elements configured to receive input from a user to configurably assign signal outputs of one or more of the three electrodes to a new limb designation; and
in response to receiving the input from the user, sending instructions to the via the communication interface to associate readings from each of the three electrodes in accordance with the input.

10. The apparatus of claim 5, further comprising a remote computing system comprising:
third program instructions stored on third computer readable storage media that, when executed by third controller, direct the third controller to:
receive the 6-lead electrocardiogram data provided from the mobile device; and
analyze the 6-lead electrocardiogram data; and
provide diagnostic information.

11. The apparatus of claim 10, further comprising program instructions stored on the second computer readable storage media that, when executed by the second controller, direct the second controller to:
receive the diagnostic information provided from the remote computing system; and
display user interface elements configured to output the diagnostic information provided from the remote computing system.

12. The apparatus of claim 1, further comprising program instructions stored on the one or more computer readable storage media that, when executed by the controller, direct the controller to perform digital signal processing on the signals received from the three electrodes, wherein the digital signal processing includes one or more of the following:
digital signal compensation for impedance variance in the signals according to electrode type and user characteristics;
linear phase filtering of the signals;
digital compensation of signal-to-noise ratio in the signals;
digital removal of baseline wander in the signals.

13. The apparatus of claim 1, wherein the housing and the attachment mechanism form a protective case for the mobile device.

14. The apparatus of claim 1, wherein the attachment mechanism comprises rails attached to the mobile device that engage with a recessed slot on the housing.

15. The apparatus of claim 1, wherein the communication interface comprises a physical communication port on the apparatus that engages with a corresponding port on the mobile device when the housing is attached to the mobile device.

16. The apparatus of claim 9, wherein the three electrodes are disposed on a single electrode pad on the single surface of the housing, and wherein the user interface elements are further configured to receive input from the user to configurably assign touch contact zones on the single electrode pad designating the signal outputs.

* * * * *